US009907777B2

(12) United States Patent
Lee et al.

(10) Patent No.: US 9,907,777 B2
(45) Date of Patent: *Mar. 6, 2018

(54) METHODS FOR TREATING BIPOLAR DISORDER

(71) Applicant: SK Biopharmaceuticals Co., Ltd., Seoul (KR)

(72) Inventors: Sung James Lee, Montville, NJ (US); Susan Marie Melnick, Parsippany, NJ (US)

(73) Assignee: SK Biopharmaceuticals Co., Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/432,479

(22) Filed: Feb. 14, 2017

(65) Prior Publication Data

US 2017/0151209 A1    Jun. 1, 2017

Related U.S. Application Data

(63) Continuation of application No. 12/827,505, filed on Jun. 30, 2010, now Pat. No. 9,610,274.

(51) Int. Cl.
*A61K 31/27* (2006.01)
*C07C 271/08* (2006.01)

(52) U.S. Cl.
CPC .................................. *A61K 31/27* (2013.01)

(58) Field of Classification Search
CPC .... A61K 31/27; A61K 31/137; A61K 31/223; C07C 271/08; C07C 271/12
See application file for complete search history.

(56) References Cited

U.S. PATENT DOCUMENTS

| | | | |
|---|---|---|---|
| 5,705,640 A | 1/1998 | Choi et al. | |
| 5,756,817 A | 5/1998 | Choi et al. | |
| 5,955,499 A | 9/1999 | Choi et al. | |
| 6,002,009 A | 12/1999 | Cereda et al. | |
| 6,140,532 A | 10/2000 | Choi et al. | |
| 7,642,261 B2 | 1/2010 | Bartoszyk et al. | |
| 8,232,315 B2 | 7/2012 | Lee et al. | |
| 8,440,715 B2 | 5/2013 | Ahnaou et al. | |
| 8,552,060 B2 | 10/2013 | Palumbo et al. | |
| 8,623,913 B2 | 1/2014 | Melnick et al. | |
| 2001/0034320 A1 | 10/2001 | Brecht et al. | |
| 2002/0151585 A1 | 10/2002 | Plata-Salaman et al. | |
| 2002/0156127 A1 | 10/2002 | Piata-Salainan et al. | |
| 2003/0153612 A1 | 8/2003 | Sethi | |
| 2004/0115263 A1 | 6/2004 | Robertson et al. | |
| 2005/0080268 A1 | 4/2005 | Choi et al. | |
| 2006/0258718 A1 | 11/2006 | Choi et al. | |
| 2007/0123519 A1 | 5/2007 | Abarghaz et al. | |
| 2007/0197657 A1 | 8/2007 | Beyreuther et al. | |
| 2008/0039529 A1 | 2/2008 | Sporn | |
| 2008/0090902 A1 | 4/2008 | Pandey et al. | |
| 2010/0093801 A1 | 4/2010 | Chung et al. | |
| 2012/0223775 A1 | 9/2012 | Kim et al. | |
| 2012/0245226 A1 | 9/2012 | Lee et al. | |
| 2012/0252892 A1 | 10/2012 | Lee et al. | |
| 2013/0137764 A1 | 5/2013 | Ahnaou et al. | |

FOREIGN PATENT DOCUMENTS

| | | |
|---|---|---|
| CN | 1135209 A | 11/1996 |
| CN | 10132787 | 2/2008 |
| CN | 101217949 A | 7/2008 |
| CN | 101557804 A | 10/2009 |
| EP | 0633023 | 1/1995 |
| JP | H09503231 | 3/1997 |
| JP | 2008518921 | 6/2008 |
| KR | 100197892 B1 | 6/1999 |
| KR | 20070083826 A | 8/2007 |
| KR | 20080035565 A | 4/2008 |
| WO | 96/07637 | 3/1996 |
| WO | 96/24577 | 8/1996 |
| WO | 96/32375 | 10/1996 |
| WO | 98/15526 | 4/1998 |
| WO | 98/017636 | 4/1998 |
| WO | 99/02494 | 1/1999 |
| WO | 99/55674 | 11/1999 |
| WO | 02/50071 | 6/2002 |
| WO | 02/080928 | 10/2002 |
| WO | 02/100352 | 12/2002 |
| WO | 2004/026868 | 4/2004 |
| WO | 2004/094418 | 11/2004 |
| WO | 2005/021539 | 3/2005 |
| WO | 2005/092882 | 10/2005 |
| WO | WO 2006/050037 A1 | 5/2006 |
| WO | 2006/106425 | 10/2006 |
| WO | 2006133393 | 12/2006 |
| WO | 2007/018496 | 2/2007 |
| WO | 2008/048801 | 4/2008 |
| WO | 2008048801 A2 | 4/2008 |
| WO | 2011/005473 | 1/2011 |

(Continued)

OTHER PUBLICATIONS

Cascade et al. "Use of Antidepressants: Expansion Beyond Depression and Anxiety", *Psychiatry* 25-28 (2007).
Griswold et al. "Manaaernent of Bipolar Disorder", *Am. Fam. Physician* 62(6):1343-1353 (2000).
Office Action form the Patent Office of the Russian Federation, Federal Institute of Industrial Property for Application No. 2012155118/15(087435) dated Oct. 24, 2016.
Hilty, D. N. et al., "A Review of Bipolar Disorder in Adults", Psychiatry, Sep. 2006, pp. 43-55.
Search Report from the State Intellectual Property Office of the People's Republic of China for Application No. 201180032698.X dated Sep. 6, 2016 (3 pages).
"Guide to Depression and Bipolar Disorder", Depression and Bipolar Support Alliance (DBSA) brochure, Nov. 2002, 17 pages, Depression and Bipolar Support Alliance, Chicago, Illinois.

(Continued)

*Primary Examiner* — Uma Ramachandran
(74) *Attorney, Agent, or Firm* — Myers Bigel, P.A.

(57) ABSTRACT

The invention is directed to a method of treating bipolar disorder in a subject, comprising administering a therapeutically effective amount of a carbamate compound, or pharmaceutically acceptable salt or amide thereof.

13 Claims, 1 Drawing Sheet

(56) References Cited

FOREIGN PATENT DOCUMENTS

| | | |
|---|---|---|
| WO | 2011/055964 | 5/2011 |
| WO | 2011/055965 | 5/2011 |

OTHER PUBLICATIONS

Lyon "Animal Models for the Symptoms of Mania," Neuromethods, vol. 18: Animal Models in Psychiatry I, 1991, pp. 197-244.
Gaineldinov et al., "Monoamine Transporters: From Genes to Behavior," Annu. Rev. Pharmacol. Toxicol. 2003, 43:261-284.
European Patent Office Examination Report for Application No. 11801093.3 dated Apr. 20, 2015 (7 pages).
Clinical psychiatry 2006, vol. 35, No. 10, p. 1467-1470.
Yalham et al., "Atypical Antipsychotics in Bipolar Depression: Potential Mechanisms of Action" J Clin Psychiaty, 2005, vol. 66[suppl 5], p. 40-48.
Office Action from the State Intellectual Property Office of the People's Republic of China for Application No. 201180032698.X dated Jun. 11, 2015 (7 pages).
Hassan et al., "How to Keep the Brain awake? The Complex Molecular Pharmacogenetics of Wake Promotion," Neuropsychopharmacology 34:1625-1640 (2009).
European Extended Search Report for Application No. 11801093.3 dated Jan. 3, 2014 (10 pages).
Gordon R. et al., "Pharmacological profile of YKP10A: a novel antidepressant", Abstracts of the annual meeting of the Society of Neuroscience, Jan. 1, 1998.
Amsterdam Jay D. et al., "A single-site, double-blind, placebo-controlled, dose-ranging study of YKP10A: A putative, new anti-depressant", Progress in Neuro-Psychopharmacology & Biological Psychiatry, Dec. 1, 2002, pp. 1333-1338.
United States Patent Office Action for U.S. Appl. No. 13/508,145 dated Apr. 15, 2013 (18 pages).
Garcia-Borreguero et al., "Treatment of restless legs syndrome with gabapentin: A double-blind, cross-over study," Neurology, 59, Nov. 2002, p. 1573-1579.
United States Patent Office Action for U.S. Appl. No. 12/827,529 dated Apr. 22, 2013 (10 pages).
European Search Report for Application No. 10828500.8 dated Mar. 12, 2013 (4 pages).
Beers, M. et al., "The Merck Manual of Diagnosis and Therapy" Merck Research Laboratories, Mar. 5, 1999, seventeenth edition, pp. 2254-2259.
European Search Report for Application No. 10828479.5 dated Mar. 21, 2013 (11 pages).
Arnold et al., "Comorbidity of Fibromyalgia and Psychiatric Disorders", J Clin Psychiatry, Aug. 2006, vol. 67, No. 8, pp. 1219-1225.
Banno et al., Sleep Medicine (2000) pp. 221-229.
Bennett et al., "A peripheral mononeuropathy in rat that produces disorders of pain sensation like those seen in man," Pain, 1988, vol. 33, pp. 87-107.
Bennett, "Clinical Manifestations and Diagnosis of Fibromyalgia," Rhuem Dis Clin N Am, 2009, vol. 35, pp. 215-232.
Cami et al., The New England Journal of Medicine (2003) Massachusetts Medical Society vol. 349, pp. 975-986.
Choy et al., "Safety and tolerability of duloxetine in the treatment of patients with fibromyalgia: pooled analysis of data from five clinical trials," Clin Rheumatol, 2009, vol. 28, pp. 1035-1044.
Daley, "Update on attention-deficit/hyperactivity disorder, Current Opinion in Pediatrics," 16:217-226, 2004.
Daughton et al., Review of ADHD Pharmacotherapies: Advantages, Disadvantages, and Clinical Pearls. J. Am. Acad. Child Adolesc. Psychiatry, 48:3, 240-248, Mar. 2009.
Gendreau et al., "Milnacipran is safe and well tolerated in the treatment of fibromyalgia syndrome," Abstract Only, 2008.
Grund et al., Behavioral and Brain Functions 2006, 2:2,1-14, 2006.
Hargreaves et al., "A new and sensitive method for measuring thermal nociception in cutaneous hyperalgesia," Pain, 1988, vol. 32, pp. 77-88.
Harris et al., "Newer treatments for fibromyalgia syndrome," Therapeutics and Clinical Risk Management, 2008, vol. 4, No. 6, pp. 1331-1342.
Kim et al., "Pregabalin for fibromyalgia: Some relief but no cure," Cleveland Clinic Journal of Medicine, Apr. 2009, vol. 76, No. 4, pp. 255-261.
Mease, "Fibromyalgia Syndrome: Review of Clinical Presentation, Pathogenesis Outcome Measures, and Treatment," The Journal of Rheumatology, 2005, vol. 32, Suppl. 75, pp. 6-21.
Murphy et al., J Clin Psychiatry 2004; 65:12-17, 2004.
Nunes et al., Journal of the American Medical Association (2004) American Medical Association, vol. 291, pp. 1887-1896.
PCT/KR2010/007603 Internatonal Search Report and Written Opinion dated July 29, 2011 (9 pages).
PCT/KR2010/007698 International Search Report and Written Opinion dated Jul. 22, 2011 (8 pages).
Rader et al., American Family Physician, vol. 79, No. 8, 657-665, 2009.
Spencer et al., vol. 79, No. 8, 3-9, 2002.
Verdu et al., "Antidepressants for the Treatment of Chronic Pain," Drugs, 2008, vol. 68, No. 18, pp. 2611-2632.
Xu et al., Bioorganic and Medicinal Chemistry (2006) Elsevier, vol. 14, pp. 3285-3299.
PCT/KR2011/004677 International Search Report dated Feb. 24 2012 (4 pages).
PCT/KR2011/004677 International Preliminary Report on Patentability dated Jan. 17, 2013 (7 pages).
Nisell, Magnus, et al., "Nicotine Dependence, Midbrain Dopamine Systems and Psychiatric Disorders", Pharmacology & Toxicology, vol. 76, pp. 157-162, 1995.
Pontieri, Francesco, E. et al., "Effects of Nicotine on the Nucleus Accumbens and Similarity to Those of Addictive Drugs" Letters to Nature, vol. 382, pp. 255-257, Jul. 18, 1996.
Damsma, Geert, et al., "Lack of Tolerance to Nicotine-Induced Dopamine Release in the Nucleus Accumbens", European Journal of Pharmacology, vol. 168, pp. 363-368, 1989.
Di Chiara, Gaetano, et al., "Drugs Abused by Humans Preferentially Increase Synaptic Dopamine Concentrations in the Mesolimbic System of Freely Moving Rats", Proc. Natl. Acad. Sci. USA, vol. 85, pp. 5274-5278, Jul. 1988.
Imperato, Assunta, et al., "Nicatine preferentially Stimulates Dopamine Release in the Limbic System of Freely Moving Rats", European Journal of Pharmacology, vol. 132, pp. 337-338, 1986.
Nissell, Magnus, et al., "Infusion of Nicotine in the Ventral Tegmental Area or the Nucleus Accumbens of the Rat Differentially Affects Accumbal Dopamine Release", Pharmacology & Toxicology, vol. 75, pp. 348-352, 1994.
Nissell, Magnus, et al., "Systemic Nicotine-Induced Dopamine Release in the Rat Nucleus Accumbens is Regulated by Nicotinic Receptors in the Ventral Tegmental Area", Synapse, pp. 36-44, 1994.
Henningfield, Jack, E. Ph.D., "Nicotine Medications for Smoking Cessation", The New England Journal of Medicine, vol. 333, No. 18, pp. 1196-1203, Nov. 2, 1995.
Hurt, Richard, D., et al, "A Comparison of Sustained-Release Bupropion and Placebo for Smoking Cessation", The New England Journal of Medicine, vol. 337, No. 17, pp. 1195-1202, Oct. 23, 1997.
PCT/KR2009/005863 International Search Report and Written Opinion dated May 28, 2010 (9 pages).
Miklowitz David, J., et al., "The Psychopathology and Treatment of Bipolar Disorder", Annu. Rev. Clin. Psychol., vol. 2, 2006.
Miller, Christopher, J., et al., "Assessment Tools for Adult Bipolar Disorder", Clin Psychol. (New York), vol. 16, No. 2, pp. 188-201, Jun. 1, 2009.
Minto, Charles, F., et al., "Pharmacokinetics and Pharmacodynamics of Nandrolone Esters in Oil Vehicle: Effects of Ester, Injection Site and Injection Volume", The Journal of Pharmacology and Experimental Therapeutics, vol. 281, No. 1, pp. 93-102, 1997.
Ostro Marc, J., et al., "Use of Liposomes as Injectable-Drug Delivery Systems", American Journal of Hospital Pharmacy, vol. 46, pp. 1576-1581, Aug. 1989.

(56) References Cited

OTHER PUBLICATIONS

Rao, K, "Recent Developments of Collagen-Based Materials for Medical Applications and Drug Delivery Systems", J. Biomater. Sci. Polymer Edn., vol. 7, No. 7, pp. 623-645, 1995.
Rapoport, Stanley, I., et al., "Bipolar Disorder and Mechanisms of Action of Mood Stabilizers", Brain Research Reviews, vol. 61, pp. 185-209, 2009.
Rohatagi, Shashank, PhD, et al., "Pharmacokinetic and Pharmacodynamic Evaluation of Triamcinolone Acetonide After Intravenous, Oral, and Inhaled Administration", J. Clin. Pharmacol., vol. 35, pp. 1187-1193, 1995.
Tjwa, Martin, K. T., MD, "Budesonide Inhaled Via Turbuhaler: A More Effective Treatment for Asthma than Beclomethasone Dipropionate Via Rotahaler", Annals of Allergy, Asthma & Immunology, vol. 75, pp. 107-111, 1995.
Vieta, Eduard, et al., "Evolving Trends in the Long-Term Treatment of Bipolar Disorder", The World Journal of Biological Psychiatry, vol. 8, No. 1, pp. 4-11, 2007.
Al-Muhammed, J., et al., "In-Vivo Studies on Dexamethasone Sodium Phosphate Liposomes", J. Microencapsulation, vol. 13, No. 3, pp. 293-306, 1996.
Azorin Jean-Michel, el al., "An Update on the Treatment of Bipolar Depression", Expert Opin. Pharmacother., vol. 10, No. 2, pp. 161-172, 2009.
Chengappa, KNR, et al., "Barriers to the Effective Management of Bipolar Disorder: A Survey of Psychiatrists Based in the UK and USA", Bipolar Disorders, vol. 7, suppl.1, pp. 38-42, 2005.
Chonn, Aracadio, et al., "Recent Advances in Liposome Drug-Delivery Systems", Current Opinion in Biotechnology, vol.6, pp. 698-708, 1995.
Cousins, David, A., et al., "The Role of Dopamine in Bipolar Disorder", Bipolar Disorders, vol. 11, pp. 787-806, 2009.
Cuellar, Amy, K., et al., "Distinctions Between Bipolar and Unipolar Depression", Clin. Psychol. Rev., vol. 25, No. 3, pp. 307-339, May 2005.
Eyles, J.E., et al., "Oral Delivery and Fate of Poly(lactic acid) Microsphere-encapsulated Interferon in Rats", J. Pharm. Pharmacol, vol. 49, pp. 669-574, 1997.
Frye, Mark, A., et al., "Unmet Needs in Bipolar Depression", Depression and Anxiety, vol. 19, pp. 1999-1208, 2004.
Gao, Zhu-Hui, et al., "Controlled Release of a Contaceptive Steroid from Biodegradable and Injectable Gel Formulations: In Vitro Evaluation", Pharmaceutical Research, vol. 12, No. 6, pp. 857-863, 1995.
Harel, Eiran Vadim, MD, et al., "Effectiveness and Safety of Adjunctive Antidepressants in the Treatment of Bipolar Depression: A Review", Isr J Psychiatry Relat Sci, vol. 45, No. 2, pp. 121-128, 2008.
Kessler, Ronald, C., et al., "Lifetime Prevalence and Age-of-Onset Distributions of DSM-IV Disorders in the National Comorbidity Survey Replication", Arch Gen Psychiatry, vol. 62, pp. 593-602 & 768, Jun. 2005.
Kessler, Ronald, C., et al., "Prevalence, Severity and Comorbidity of Twelve-month DSM-IV Disorders in the National Comorbidity Survey Replication (NCS-R)", Arch Gen Psychiatry, vol. 62, No. 6, pp. 617-627, Jun. 2005.
Bayard, Max, MD, et al., "Restless Legs Syndrome", American Family Physician, vol. 78, No. 2, pp. 235-240, Jul. 15, 2008.
Ferini-Strambi, Luigi, "Treatment Options for Restless Legs Syndrome" Expert Opin. Pharmacother., vol. 10, No. 4, pp. 545-554, 2009.
Fulda, Stephany, et al., "Dopamine Agonists for the Treatment of Restless Legs Syndrome", Expert Opin. Pharmacother., vol. 6, No. 15, pp. 2655-2666, 2005.
Garcia-Borreguero, Diego, MD, et al., "Circadian Variation in Neuroendocrine Response to L-dopa in Patients with Restless Legs Syndrome", Sleep, vol. 27, No. 4, pp. 669-673, 2004.
Hornyak, Magdolna, "Depressive Disorders in Restless Legs Syndrome", CNS Drugs. vol. 24, No. 2, pp. 89-98, 2010.
Kim, Sung-Wan, MD, et al., "Bupropion May Improve Restless Legs Syndrome", Clin Neuropharmacol, vol. 28, No. 6, pp. 298-301. Nov.-Dec. 2005.
Ondo, William, G., MD, "Restless Legs Syndrome", Neurol Clin, vol. 27, pp. 779-799, 2009.
Stiasny-Kolster, K., et al., "Static Mecanical Hyperalgesia Without Dynamic Tactile Allodynia in Patients with Restless Legs Syndrome", Brain, vol. 127, No. 4, pp. 773-782, 2004.
Allen. R.P., PhD, et al., "MRI Measurement of Brain Iron in Patients with Restless Legs Syndrome", Neurology, vol. 56, pp. 263-265, Jan. 2001.

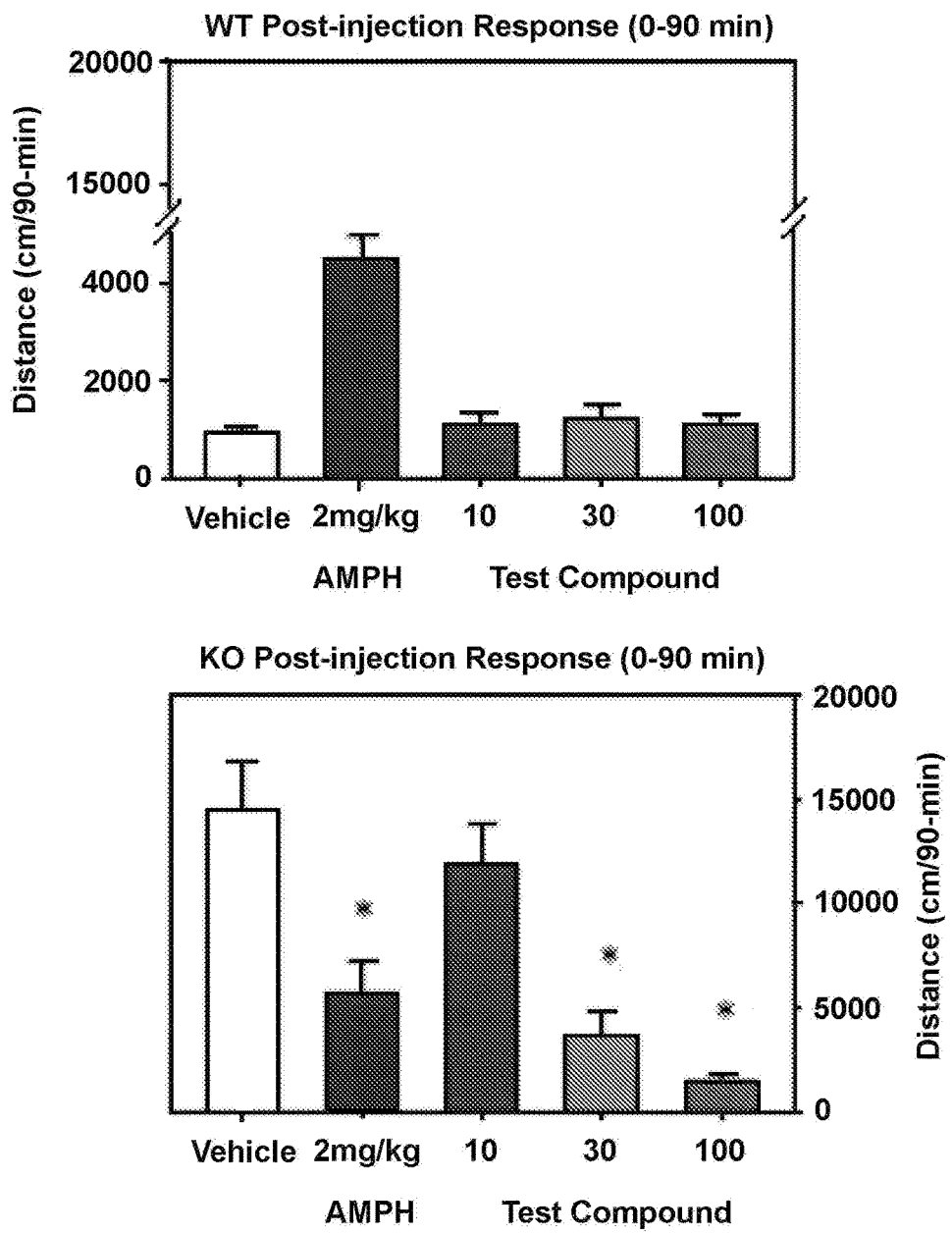

METHODS FOR TREATING BIPOLAR DISORDER

RELATED APPLICATIONS

This application is a continuation of and claims priority to U.S. patent application Ser. No. 12/827,505, filed Jun. 30, 2010, the entire contents of which is incorporated by reference herein.

BACKGROUND OF THE INVENTION

The present invention relates a method of treating bipolar disorder. More specifically, the present invention is directed to a method of using a carbamate compound alone or in combination with other medications, for the treatment of bipolar disorder.

DESCRIPTION OF RELATED ART

Bipolar Disorder (BPD) is a chronic and cyclic psychiatric disorder characterized by mania and depression. Bipolar I disorder is qualified by at least one lifetime manic or mixed episode (Miklowitz & Johnson, 2009). Mania must last at least one week or require hospitalization and symptoms during this period include irritability, euphoria, decreased need for sleep, grandiose ideas, impulsive behavior, increased talkativeness, racing thoughts, increased activity and distractibility. A mixed episode includes manic symptoms along with a simultaneous depression. Bipolar II consists of periods of hypomania and major depression. Hypomania is similar to mania but considered milder in that the patient is not socially or vocationally impaired but shows changes in functioning (Miller et al., 2009). During major depression, the patient experiences intense feelings of sadness/worthlessness, loss of interests, fatigue, insomnia, agitation, weight gain/loss and suicidal ideation/attempts. Lifetime prevalence rate is estimated at approximately 4% based upon the National Comorbidity Survey replication (Kessler et al., 2005a). There is high comorbidity of bipolar disorder with attention hyperactivity disorder and substance abuse among others (Kessler et al., 2005b).

Treatment of bipolar disorder is aimed at treating the manic, hypomanic and depressive symptoms of the disorder as well, as at maintaining treatment by reducing or preventing the cyclicity of the disorder. Lithium has long been considered the standard treatment of bipolar disorder based on a few early clinical trials which have since been highly criticized for methodological issues (Vieta & Rosa, 2007). Nevertheless, lithium unquestionably is efficacious for mania but less so in treating depression (Frye et al., 2004). In addition, patients treated with lithium can show some signs of illness, abrupt cessation of treatment can induce a manic episode and further not all can tolerate the treatment (Vieta & Rosa, 2007). Carbamazepine and valproate may also be beneficial for BPD but additional long-term clinical studies are necessary (Azorin & Kaladjian, 2009). Second generation antipsychotics including olanzapine, quetiapine, risperidone and clozapine have shown some promise in the treatment of BPD but side effects including sedation, weight gain and metabolic disorders are common (Vieta & Rosa, 2007). Antidepressants, fluoxetine, paroxetine and venlafaxine show some efficacy in the treatment of bipolar depression (Hard & Levkovitz, 2008; Azorin & Kaladjian, 2009). However, switch rate defined as the change from depression to mania or hypomania is reported to be increased for antidepressants especially venlafaxine but there was no consistency in what constituted a switch and how dropouts from placebo groups were handled. Cycle acceleration or rapid cycling is another risk associated with antidepressant treatment in BPD (Harel & Levkovitz, 2008). Similar to switch rate, there a lack of a consistent definition and controlled data on cycle acceleration. Thus, more controlled studies with, systematic and objective measures are needed to adequately assess the incidence of these risks.

There appears to be an implication of dopamine in bipolar disorder (Cuellar et al., 2005; Cousins et al., 2009; Rapoport et al., 2009). While the role is complex, the use of stimulants such as amphetamine tends to mimic bouts of mania. On the other hand, dopamine agonists alleviate the apparent dopamine deficiency observed in Parkinson's disease-induced depression. Untreated bipolar depressive patients showed decreased levels of the dopamine metabolite, homovanillic acid (HVA), in the cerebrospinal fluid. Dopaminergic agents should be sought to provide a balance in the dopaminergic neurosystems in order to prevent the extreme cycling between mania and depression in BPD. There also has been reported to be an imbalance of norepinephrine in bipolar disorder (Cueller et al., 2005).

In a survey of psychiatrists in the UK and US, high unmet, needs in BPD were identified (Chengappa & Williams, 2005). Underserved subsets of BPD were those patients who are rapid cyclers and those with comorbid substance abuse. It was felt that BPD would benefit by treatment that was better tolerated and effective in all phases of the disease with reduced relapse frequency and a fast onset of action.

Accordingly, there is a need manic and depressive episodes and other comorbidities including attention-hyperactivity disorder and substance abuse and reduce side effect profiles.

SUMMARY OF THE INVENTION

The present invention is directed to a method of treating bipolar disorder comprising the administration of a therapeutically effective amount of a compound having structural Formula (1) or a pharmaceutically acceptable salt thereof, to a mammal in need of the treatment:

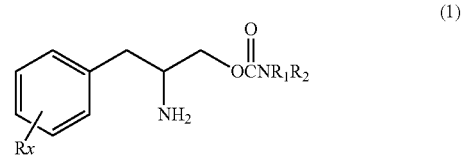

(1)

wherein,

R is selected from the group consisting of hydrogen, lower alkyl of 1 to 8 carbon atoms, halogen selected from F, Cl, Br and I, alkoxy of 1 to 3 carbon atoms, nitro group, hydroxy, trifluoromethyl, and thioalkoxy of 1 to 3 carbon atoms;

x represents the number of R, and, is an integer of 1 to 3, with the proviso that R may be the same or different when x is 2 or 3;

$R_1$ and $R_2$ can be the same or different from each other and are independently selected from the group consisting of hydrogen, lower alkyl of 1 to 8 carbon atoms, aryl of 3 to 7 carbon atoms, arylalkyl of 3 to 7 carbon atoms, and cycloalkyl of 3 to 7 carbon atoms;

$R_1$ and $R_2$ can be joined to form a 5 to 7-membered heterocycle substituted with a member selected from the group consisting of hydrogen, alkyl of 1 to 8 carbon atoms, and aryl of 3 to 7 carbon atoms, wherein the heterocyclic compound comprises 1 to 2 nitrogen atoms and 0 to 1 oxygen atom, and the nitrogen atoms are not directly connected with each other or with the oxygen atom.

In another embodiment, the present invention provides a method of improving symptoms associated with bipolar disorder in a subject, comprising the step of the administration, to a subject in need of such treatment, of a therapeutically effective amount a compound of the Formula (1) or a pharmaceutically acceptable salt thereof.

In further embodiment, the present invention provides a method of ameliorating or eliminating symptoms of bipolar disorder in a subject, comprising the step of the administration, to a subject in need of such treatment, of a therapeutically effective amount a compound of the Formula (1) or a pharmaceutically acceptable salt thereof.

In additional embodiment, the present invention is directed to a pharmaceutical composition for treating bipolar disorder comprising a compound of the Formula (1) or a pharmaceutically acceptable salt thereof, as an active ingredient.

In another embodiment, the present invention provides a pharmaceutical composition for improving symptoms associated with bipolar disorder in a subject, comprising a compound of the Formula (1) or a pharmaceutically acceptable salt thereof, as an active ingredient.

In further embodiment, the present invention, provides a pharmaceutical composition for ameliorating or eliminating symptoms of bipolar disorder in a subject, comprising a therapeutically effective amount a compound of the Formula (1) or a pharmaceutically acceptable salt thereof.

The compound having structural Formula (1) is an enantiomer substantially free of other enantiomers or an enantiomeric mixture wherein one enantiomer of the compound having structural Formula (1) predominates. One enantiomer predominates to the extent of about 90% or greater, and preferably about 98% or greater.

The enantiomer is (S) or (L) enantiomer as represented by Struetural Formula (1a) or (R) or (D) enantiomer, as represented by Structural Formula (1b):

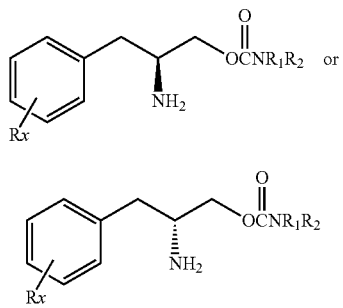

Preferably, R, $R_1$ and $R_2$ are all selected from hydrogen, which are shown in the following formula:

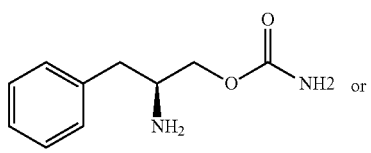

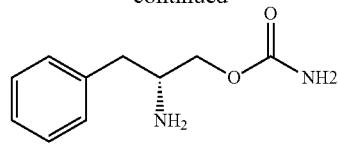

Embodiments of the invention include a method for using the enantiomer of Formula 1 substantially free of other enantiomers that is the enantiomer of Formula 1b or an enantiomeric mixture wherein the enantiomer of Formula 1b predominates. (Note: in the structural formula of Formula 1b below the amino group attached to the beta carbon projects into the plane of the paper. This is the dextrorotary (D) enantiomer that is of absolute configuration (R).)

DETAILED DESCRIPTION OF THE EMBODIMENT

These and other objects of the invention will be more fully understood from the following description of the invention and the claims appended hereto.

The present invention is directed to a method of treating bipolar disorder comprising the administration of a therapeutically effective amount of a compound having structural Formula (1) or enantiomers, diastereomers, racemates or mixtures thereof, or hydrates, solvates and pharmaceutically acceptable salts and amides thereof; to a mammal in need of the treatment:

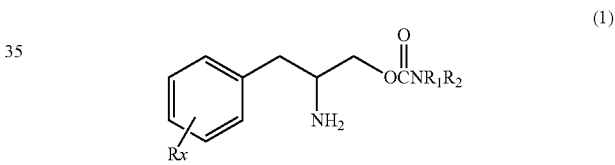

wherein,

R is selected from the group consisting of hydrogen, lower alkyl of 1 to 8 carbon atoms, halogen selected from F, Cl, Br and I, alkoxy of 1 to 3 carbon atoms, nitro group, hydroxy, trifluoromethyl, and thioalkoxy of 1 to 3 carbon atoms;

x represents the number of R, and is an integer of 1 to 3, with the proviso that R may be the same or different when x is 2 or 3;

$R_1$ and $R_2$ can be the same, or different from each other and are independently selected from the group consisting of hydrogen, lower alkyl of 1 to 8 carbon atoms, aryl of 3 to 7 carbon atoms, arylalkyl of 3 to 7 carbon atoms, and cycloalkyl of 3 to 7 carbon atoms;

$R_1$ and $R_2$ can be joined to form a 5 to 7-membered heterocycle substituted with a member selected from the group consisting of hydrogen, alkyl of 1 to 8 carbon atoms, and aryl of 3 to 7 carbon atoms, wherein the heterocyclic compound comprises 1 to 2 nitrogen atoms and 0 to 1 oxygen atom, and the nitrogen atoms are not directly connected with each other or with the oxygen atom.

The present method also includes the use of a compound selected from the group consisting Formula 1a or 1b, or enantiomers, diastereomers, racemates or mixtures thereof, or hydrates, solvates and pharmaceutically acceptable salts and amides thereof:

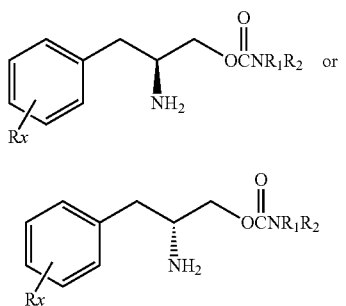

(1a) or (1b)

wherein Rx, $R_1$ and $R_2$ are the same as defined above.

The present method also preferably includes the use of the D (or dextrorotary) enantiomer (of absolute configuration R) selected from the group consisting of a compound of Formula 1 or an enantiomeric mixture thereof. In the structural formula of Formula 1b, the amino group attached to the beta carbon projects into the plane of the paper. This is the dextrorotary (D) enantiomer that is of absolute configuration (R).

Preferably, in the Structural Formula 1, R, $R_1$ and $R_2$ are hydrogen as represented by following Structural Formula:

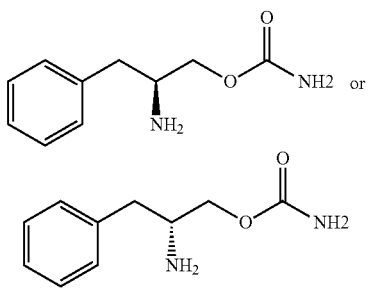

O-carbamoyl-(D)-phenylalaninol is also named (R)-(beta-amino-benzenepropyl) carbamate monohydrochloric acid. For enantiomeric mixtures, wherein O-carbamoyl-(D)-phenylalaninol predominates, preferably, to the extent of about 90% or greater, and more preferably about 98% or greater.

The compounds of Formula 1 can be synthesized by methods known to a skilled person in the art. Some reaction schemes for synthesizing compounds of Formula (1) have been described in published; U.S. Pat. No. 5,705,640, U.S. Pat. No. 5,756,817, U.S. Pat. No. 5,955,499, and U.S. Pat. No. 6,140,532. Details of the above reactions schemes as well as representative examples on the preparation of specific compounds have been described m published; U.S. Pat. No. 5,705,640, U.S. Pat. No. 5,756,817, U.S. Pat. No. 5,955,499, U.S. Pat. No. 6,140,532, all incorporated herein by reference in their entirety.

The salts and amides of the compounds of Formula (1) can be produced by treating the compound with an acid (HX) in suitable solvent or by means well known to those of skill in the art.

From Structural Formula 1, it is evident that some of the compounds of the invention have at least one and possibly more asymmetric carbon atoms. It is intended that the present invention include within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999 The protecting groups may be removed at a convenient subsequent stage using methods known from the art.

The present invention is based in part on the discovery that phenylalkylamino carbamates of Formula 1 discussed above have novel and unique pharmacological properties. These compounds have been shown in several animal models to have the ability to treat bipolar disorder and improve, ameliorate or eliminate symptoms associated with bipolar disorder.

Although the precise mechanism of action is not completely understood, it is known that these compounds do not work by the same mechanisms as most other known treatments for bipolar disorder. For these reasons, the compounds of Formula 1 are especially suitable for use as sole or adjunctive treatment for bipolar disorder and improvement, amelioration or elimination of symptoms associated with bipolar disorder.

Thus, these compounds can be safely used alone or in combination with other useful medications to provide enhanced efficacy and reduced side effects because smaller doses of each drug that could be used.

In one aspect, this invention relates to methods to treat bipolar disorder; the method comprising administering to a subject suffering from bipolar disorder a therapeutically effective amount of one or more of the carbamate compounds of the invention or a pharmaceutically acceptable, salt or amides thereof, optionally with a pharmaceutically acceptable carrier, diluent or excipient. The method may further comprise the step of identifying a subject suffering from bipolar disorder before the administering step.

In another aspect, this invention also provides, a method for diminishing, inhibiting or eliminating the symptoms associated with bipolar disorder including manic (e.g., unrealistic plans, spending sprees, recklessness, decreased need for sleep, pressured speech, inflated self-esteem, uncharacteristically poor judgment, indifferent to personal grooming and unusual sexual drive) and depressive (sadness and crying spells, hypersomnolence insomnia, anorexia, excessive eating and may gain weight, loneliness, self-loathing, apathy or indifference, depersonalization, loss of interest in sexual activity, shyness or social anxiety, chronic pain, lack of motivation, morbid/suicidal ideation, irritability or restlessness) symptoms in a subject suffering from bipolar disorder which comprises administering to the subject an effective amount of carbamate compounds of the invention, a pharmaceutically acceptable salt, or amides thereof to diminish, inhibit or eliminate said symptoms.

Definitions

For convenience, certain terms employed in the specification, examples, and appended claims are collected here.

It is to be understood that this invention is not limited to the particular methodology, protocols, animal species or genera, and reagents described, as such may vary. It is also to be understood that the terminology used herein is for the purpose of describing particular embodiments only, and is not intended to limit the scope of the present invention that will be limited only by the appended claims.

As used herein the term "subject", refers to an animal, preferably a mammal, and most preferably a human both male and female, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of one or more of the signs or symptoms of the disease or disorder being treated.

The term "prophylactically effective amount" is intended to mean that amount of a pharmaceutical drug that will prevent or reduce the risk of occurrence of the biological or medical event that is sought to be prevented of a tissue, a system, animal or human that is being sought by a researcher, veterinarian, medical doctor or other clinician.

The term "pharmaceutically acceptable salts or amides" shall mean non-toxic salts or amides of the compounds employed in this invention which are generally prepared by reacting the free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochloride: edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, Iactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, militate, tartrate, teoclate, tosylate, triethiodide, valerate.

Therefore, the term "a patient in need of treatment" as used herein will refer to any subject or patient who currently has or may develop any of the above syndromes or disorders, including any mood disorder which can be treated by antidepressant medication, or any other disorder in which the patient's present clinical condition or prognosis could benefit from the administration of one or more compounds of Formula (1) alone or in combination with another therapeutic intervention including but not limited to another medication.

The term "treating" or "treatment" as used herein, refers to any indicia of success in, the prevention or amelioration of an injury, pathology or condition of bipolar disorder and modification or symptoms of bipolar disorder, including any objective or subjective parameter such as abatement; remission; diminishing of symptoms or making the injury, pathology, or condition more tolerable to the patient; slowing in the rate of degeneration or decline or worsening of the illness; making the final point of worsening less debilitating; or improving a subject's physical or mental well-being. The treatment or amelioration of symptoms can be based on objective or subjective parameters; including the results of a physical examination, neurological examination, and/or psychiatric evaluations. Accordingly, the term "treating" or "treatment" includes the administration of the compounds or agents of the present invention, for treatment of any form of bipolar disorder in both males and females. In some instances, treatment with the compounds of the present mention will done in combination with other compounds to prevent, inhibit, or arrest the progression of bipolar disorder.

The term "therapeutic effect" as used herein, refers to the effective improvement in or reduction of symptoms of bipolar disorder. The term "a therapeutically effective amount" as used herein means, a sufficient amount of one or more of the compounds of the invention to produce a therapeutic effect, as defined above, in a subject or patient in need of such bipolar disorder treatment.

The terms "subject" or "patient" are used herein interchangeably and as used herein mean any mammal including but not limited to human beings including a human patient or subject to which the compositions of the invention can be administered. The term mammals include human patients, both male and female and non-human primates, as well as experimental animals such as rabbits, rats, mice, and other animals.

Methods are known in the art for determining therapeutically and prophylactically effective doses for the instant pharmaceutical composition. For example, the compound can be employed at a daily dose in the range or about 0.1 mg to 400 mg usually on a regimen of several times, for example, 1 to 2 times per day, for an average adult human. The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound may be administered to a subject, by any conventional route of administration, including, but not limited to, intravenous, oral, subcutaneous, intramuscular, intradermal and parenteral. Depending on the route of administration, compounds of Formula (1) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions and suspensions.

To prepare the pharmaceutical compositions of this invention, one or more compounds of formula (1) or salt thereof as the active ingredient is intimately admixed with a pharmaceutical carrier according to conventional pharmaceutical compounding techniques. Carriers are necessary and inert pharmaceutical excipients, including, but not limited to, binders, suspending agents, lubricants, flavorings, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the Re. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over, the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The active drug can also be administered in the form or liposome delivery systems, such as small unilamellar vesicles, large urilamellar vesicles and multilamellar vesicles. Liposomes can be formed from a variety of phospholipids, such as cholesterol, stearylamine or phosphatidylcholines.

Active drag may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Preferably these compositions are in unit dosage forms, such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation.

Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 25 to about 400 mg of the active ingredient. Preferably, the range is from about 50 to about 200 mg of the active ingredient.

In some embodiments of the present invention carbamate compounds suitable for use in the practice of this invention will be administered either singly or concomitantly with at least one or more other compounds or therapeutic agents. In these embodiments, the present invention provides methods to treat bipolar disorder and modification of symptoms associated with bipolar disorder m a patient. The method includes the step of administering to a patient in need of treatment, an effective amount of one of the carbamate compounds disclosed herein in combination with an effective amount of one or more other compounds or therapeutic agents.

It is understood that substituents and substitution patterns on the compounds of the present invention can be selected by one of ordinary skill in the art to provide compounds that are chemically stable and that can be readily synthesized by techniques known in the art as well, as the methods provided herein.

The present invention includes the use of isolated enantiomers of Formula 1. In one preferred embodiment, a pharmaceutical composition comprising the isolated S-enantiomer of Formula 1 is used to provide bipolar disorder treatment in a subject. In another preferred embodiment, a pharmaceutical composition comprising the isolated R-enantiomer of Formula 1 is used to provide bipolar disorder treatment a subject.

The present invention also includes the use of mixtures of enantiomers of Formula 1. In one aspect of the present invention, one enantiomer will predominate. An enantiomer that predominates in the mixture is one that is present in the mixture in, an amount greater than any of the other enantiomers present in the mixture, e.g., in an amount greater than 50%. In one aspect, one enantiomer will predominate to the extent of 90% or to the extent of 91%, 92%, 93%, 94%, 95%, 96%, 97% or 98% or greater. In one preferred embodiment, the enantiomer that predominates in a composition comprising a compound of Formula 1 is the S-enantiomer of Formula 1.

The present invention provides methods of using enantiomers and enantiomeric mixtures of compounds represented by Formula 1, to treat bipolar disorder. A carbamate enantiomer of Formula 1 contains an asymmetric chiral carbon at the benzylic position, which is the second aliphatic carbon adjacent to the phenyl ring.

An enantiomer that is isolated is one that is substantially free of the corresponding enantiomer. Thus, an isolated enantiomer refers to a compound that is separated via separation techniques or prepared free of the corresponding enantiomer. The term "substantially free," as used herein, means that the compound is made up of a significantly greater proportion of one enantiomer. In preferred embodiments, the compound includes at least about 90% by weight of a preferred enantiomer. In other embodiments of the invention, the compound includes at least about 99% by weight of a preferred enantiomer. Preferred enantiomers can be isolated from racemic mixtures by any method known to those skilled in, the art, including high performance liquid chromatography (HPLC) and the formation and crystallization of chiral salts, or preferred enantiomers can be prepared by methods described herein.

Carbamate Compounds as Pharmaceuticals:

The present invention provides racemic mixtures, enantiomeric mixtures and isolated enantiomers of Formula 1 as pharmaceuticals: The carbamate compounds are formulated as pharmaceuticals to provide anti-bipolar disorder action in a subject.

In general, the carbamate compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intacerebroventricular, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: *Remington's Pharmaceutical Sciences,* 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The carbamate compounds can be provided as aqueous suspensions. Aqueous suspensions of the invention can contain a carbamate compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product or an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, and subcutaneous routes, can include aqueous and non-aqueous, isotonic sterile injection solutions, which car contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be, made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents. e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol. The formulations of commends can be presented in unit-dose or multi-dose sealed containers, such as ampoules and vials. Injection solutions and suspensions can be prepared from sterile powders, granules, and tablets of the kind previously described.

A carbamate compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 0.000001 percent by weight (% w) to 50% w of the carbamate compound, preferably 0.00001% w to 25% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solution, such as an effective amount of the pharmaceutical formulation suspended in, a diluents, such as water, saline or polyethyleneglycol (PEG) 400, (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethyl-cellulose; and gums including arabic and tragacanth; as well as proteins such as gelatin and collagen.

If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol, 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

In another embodiment, the compounds of the present invent on can be delivered by, the use of liposomes which fuse with the cellular membrane or are endocytosed, i.e., by employing ligands attached to the liposome that bind to surface membrane protein receptors of the cell resulting in endocytosis. By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Curr. Opin. Biotechnol. 6:698-708, 1995; Ostro, Am. Hasp. Pharm. 46:1576-1587, 1989).

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

Pharmaceutically acceptable salts refer to salts that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified air esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula (1). More than one crystal form of an enantiomer of Formula 1 can exist and as such are also included in the present invention.

A pharmaceutical composition of the invention can optionally contain, in addition to a carbamate compound, at least one other therapeutic agent useful in the treatment of bipolar disorder. For example, the carbamate compounds of Formula 1 can be combined physically with other bipolar disorder treatments in fixed dose combinations to simplify their administration.

Methods of formulating pharmaceutical compositions have been described in numerous publications such as *Pharmaceutical Dosage Forms: Tablets*, Second Edition. Revised and Expanded. Volumes 1-3, edited by Lieberman et al; *Pharmaceutical Dosage Forms*: Parenteral Medications. Volumes 1-2, edited by Avis et al; and *Pharmaceutical Dosage Forms: Disperse Systems*. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Dosage Regimens

The present invention provides methods of providing anti-bipolar disorder action in a mammal using carbamate compounds. The amount of the carbamate compound necessary to reduce or treat bipolar disorder is defined as a therapeutically or a pharmaceutically effective dose. The dosage schedule and amounts effective for this use, i.e., the dosing or dosage regimen will depend on a variety of factors including the stage of the disease, the patient's physical status, age and the like. In calculating the dosage regimen for a patient, the mode of administration is also taken into account.

A person of ordinary skill in the art will be able without undue experimentation, having regard to that skill and this disclosure, to determine a therapeutically effective amount of a particular substituted, carbamate compound for practice of this invention (see, e.g., Lieberman, Pharmaceutical Dosage Forms (Vols. 1-3, 1992); Lloyd, 1999, The art, Science and Technology of Pharmaceutical Compounding; and Pickar, 1999, Dosage Calculations). A therapeutically effective dose is also one in which any toxic or detrimental side effects of the active agent that is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

For treatment purposes, the compositions or compounds disclosed herein can be administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the carbamate compounds can include repeated doses within a prolonged treatment regimen that will yield clinically significant results to treat bipolar disorder. Determination of effective dosages in this context is typically based on animal model studies followed up by human clinical trials and is guided by determining effective dosages and administration protocols that significantly reduce the occurrence or seventy of targeted exposure symptoms or conditions in the subject. Suitable models in this regard include, for example, marine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 10 mg to about one gram or more, for single or multiple daily administration, according to the particular need of the patient By initiating the treatment regimen with a minimal daily dose of about one gram, the blood levels of the carbamate compounds can be used to determine whether a larger or smaller dose is indicated.

Effective administration of the carbamate compounds of this invention can be administered, for example, at an oral or parenteral dose of from about 0.01 mg/kg/dose to about 150 mg/kg/dose. Preferably, administration will be from about 0.1 mg/kg/dose to about 25 mg/kg/dose, more preferably from about 0.2 to about 18 mg/kg/dose. Therefore, the therapeutically effective amount of the active ingredient contained per dosage unit as described herein can be, for example, from about 1 mg/day to about 7000 mg/day for a subject having, for example, an average weight of 70 kg.

The methods of this invention also provide for kits for use in providing treatment of bipolar disorder. After a pharmaceutical composition comprising one or more carbamate compounds of this invention, with the possible addition of one or more other compounds of therapeutic benefit, has been formulated in a suitable carrier, it can be placed in an appropriate container and labeled for providing bipolar disorder treatment. Additionally, another pharmaceutical comprising at least one other therapeutic agent useful in the bipolar disorder treatment can be placed in the container as well and labeled for treatment of the indicated disease. Such labeling can include, for example, instructions concerning the amount, frequency and method of administration of each pharmaceutical.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration not limitation. The following examples are provided to illustrate specific aspects of the invention and are not meant to be limitations.

A better understanding of the present invention may be obtained in light of the following examples that are set forth to illustrate, but are not to be construed to limit, the present invention.

BRIEF DESCRIPTION OF DRAWINGS

FIG. 1 shows the influence of the tested compound on spontaneous activity (distance traveled) in mice.

EXAMPLE 1

O-carbamoyl-(D)-phenylalaninol (hereinafter, referred to 'test compound') was tested for the effects on the forced swimming test, an animal model of depression, in both mice and rats. After single doses of the test compound the mean duration of immobility was reduced with an $ED_{50}$ (median effective dose) of 16.6 mg/kg PO (per os) in mice and 18.5 mg/kg PO in rats. The test compound was even more potent after multiple dosing in mice with an $ED_{50}$ of 5.5 mg/kg PO. These data suggest that the test compound shows antidepressant properties.

(Methods)

Male CD-1 mice (16-24 g) and male Wistar rats (90-125 g) were utilized in these experiments. The test compound (10, 15 and 30 mg/kg) was dissolved in physiological saline (0.9%) and administered orally in a volume of 1 mL/100 g body weight.

Mice and rats were placed in glass cylinders of 1000 ml beakers (height 14 cm, diameter 11.5 cm) and 4000 ml beakers (height 24.5 cm, diameter 18.0 cm), respectively, containing water (25 degrees Celsius) up to a height of 9.0 cm for mice and 19.0 cm for rats. Each mouse or rat was placed in the glass cylinder and allowed to swim for 2 minutes, following which, they were observed for a period of 4 minutes for signs of immobility. Immobility was defined as lack of movement, such as floating in the water with little or no movement of hind legs. Duration of immobility was timed with a stopwatch and recorded. In some experiments, mice or rats were allowed to swim for 6 or 10 minutes, respectively, one day prior to the forced swimming experiment.

In the single dose test, mice or rats were given test compound or 0.9% NaCl and placed in glass cylinders 1 hour or 4 hours post-treatment, respectively. In the multiple dose experiments, mice were dosed twice a day for 3 days and given an additional dose on Day 4. In addition, the mice were placed in the glass cylinders containing water at 25 degrees Celsius and allowed to swim for six minutes on Day 3. Statistical evaluation was performed using a computer program (The Pharmacological Calculation System of Tallarida and Murray (#425475-04-7-1992)) based on probit analysis. Statistical significance was determined using Student's t-test at a P value of <0.05.

(Results)

The test compound, administered in a single dose, to mice reduced mean duration of immobility in a dose-dependent manner for doses of 10, 15 and 30 mg/kg PO. 10 mg/kg of the test compound reduced the mean duration of immobility to 101 sec compared to 131 sec for control (with 0.9% NaCL only). Doses of 15 and 30 mg/kg produced significant reductions of mean immobility:time from 154 sec (control) to 80 sec and from 132 sec (control) to 30 see, respectively. The $ED_{50}$ value (50% reduction in mean immobility time) for the test compound was 16.6 mg/kg.

The test compound, after multiple dosing, to mice reduced mean duration of immobility in a dose-dependent manner for doses of 3, 5 and 8 mg/kg PO. At 3 mg/kg of test compound, mean duration of immobility was reduced to 63 sec from 85 sec for control. Doses of 5 and 8 mg/kg produced significant reductions of mean immobility time from 136 sec (control) to 73 sec and from 114 sec (control) to 39 sec, respectively. The $ED_{50}$ value for the test compound was 5.5 mg/kg PO.

In rats, the test compound administered at 30 mg/kg significantly reduced mean duration of immobility from 38 sec (control) to 9 sec at 4 hours post-treatment. Doses of test compound at 10 and 15 mg/kg also reduced duration of immobility from 74 sec (control) to 62 sec and 65 sec (control) to 39 sec, respectively, but these differences were not statistically significant. The $ED_{50}$ was 18.5 mg/kg PO which is similar to the $ED_{50}$ value in mice above.

Mice administered antidepressant compounds show reduction of the mean duration of immobility compared to control as measured in the forced swim test. Thus, compounds that are active in the mouse forced swim test may show antidepressant propertied and could alleviate the depressive symptoms of bipolar disorder.

EXAMPLE 2

The test compound was tested for binding to the dopamine, norepinephrine and serotonin transporters and for the effects on dopamine, norepinephrine and serotonin reuptake. The test compound showed weak binding to the dopamine and norepinephrine transporter and weak effects on dopamine and norepinephrine reuptake compared to cocaine.

(Methods)

The test compound was weighed and dissolved in DMSO (dimethyl sulfoxide) to make a 10 or 100 mM stock solution. An initial dilution to 50 or 508 µM in assay buffer for binding, or to 1 or 10 mM in assay buffer for uptake, was made. Subsequent dilutions were made with assay buffer supplemented with DMSO, maintaining a final concentration of 0.1% DMSO. Pipetting was conducted using a Biomek 2000 robotic workstation. The concentrations of the test compounds are shown in following Table 1.

TABLE 1

Concentrations of Test Compound tested

| | Assay | Concentration Range |
|---|---|---|
| Binding | hDAT (human dopamine transporter) | 21.6 nM-100 µM |
| | hSERT (human serotonin transporter) | 21.6 nM 100 µM |
| | hNET (human norepinephrine transporter) | 21.6 nM-10 µM |
| Uptake | hDAT (human dopamine transporter) | 31.6 nM-10 µM |
| | hSERT (human serotonin transporter) | 31.6 nM-100 µM |
| | hNET (human norepinephrine transporter) | 31.6 nM-100 µM |

Inhibition of Radioligand Binding of [$^{125}$I]RTI-55 to hDAT, hSERT or hNET in Clonal Cells:

Cell Preparation:

HEK293 cells (American Type Culture Collection, ATCC) expressing hDAT, hSERT or hNET inserts are grown to 80% confluence on 150 mm diameter tissue culture dishes in a humidified 10% $CO_2$ environment at 37° C. and served as the tissue source. HEK-hDAT and HEK-hSERT cells were incubated in Dulbecco's modified Eagle's medium supplemented with 5% fetal bovine serum, 5% calf bovine serum, 0.05 U penicillin/streptomycin and puromycin (2 µg/mL). HEK-hNET cells were incubated in Dulbecco's modified Eagle's medium supplemented with 10% fetal bovine serum, 0.05 U penicillin/streptomycin and geneticin (300 µg/mL). Cell membranes are prepared as follows. Medium is poured off the plate, and the plate is washed with 10 ml of calcium- and magnesium-free phosphate-buffered saline. Lysis buffer (10 ml; 2 mM HEPES with 1 mM EDTA) is added. After 10 min, cells are scraped from plates, poured into centrifuge tubes, and centrifuged 30,000×g for 20 min. The supernatant fluid is removed, and the pellet is resuspended in 12-32 ml of 0.32 M sucrose using a Polytron at setting 7 for 10 sec. The resuspension volume depends on the density of binding sites within a cell line and is chosen to reflect binding of 10% or less of the total radioactivity.

Assay Conditions:

Each assay tube contains 50 µl of membrane preparation (about 10-15 µg of protein) prepared as above, 25 µl of test compound, compound used to define non-specific binding (mazindol or imipramine), or buffer (Krebs-HEPES, pH 7.4; 122 mM NaCl, 2.5 mM CaCl2, 1.2 mM MgS04, 10 µM pargyline, 100 µM tropolone, 0.2% glucose and 0.02% ascorbic acid, buffered with 25 mM HEPES), 25 µl of [$^{125}$I]RTI-55 ((−)-2β-Carbomethoxy-3β-(4-iodophenyl)tropane, iometopane, 40-80 pM final concentration) and additional buffer (Krebs-HEPES) sufficient to bring up the final volume to 250 µl. Membranes are preincubated with the test compound for 10 min at 25° C. prior to the addition of the [$^{125}$I]RTI-55, The assay tubes are incubated at 25° C. for 90 min. Binding is terminated by filtration over GF/C filters using a Tomtec 96-well cell harvester. Filters are washed for six seconds with ice-cold saline. Scintillation fluid is added to each square and radioactivity remaining on the filter is determined using a Wallac µ- or beta-plate reader. Specific binding is defined as the difference in binding observed in the presence and absence of 5 µM mazindol (HEK-hDAT and HEK-hNET) or 5 µM imipramine (HEK-hSERT). Two or three independent competition experiments are conducted with duplicate determinations. GraphPAD Prism is used to analyze the ensuing data, with $IC_{50}$ values convened to $K_i$ values using the Cheng-Prusoff equation ($K_i=IC_{50}/(1+([RTI-55]/K_d;RTI-55))$).

Filtration Assay for Inhibition of [$^3$H]Neurotransmitter Uptake in HEK293 Cells Expressing Recombinant Biogenic Amine Transporters:

Cell Preparation:

Cells are grown to confluence as, described above. The medium is removed, and cells are washed twice with phosphate buffered saline (PBS) at room temperature. Following the addition of 3 ml Krebs-HEPES buffer, the plates are warmed in a 25° C. water bath for 5 min. The cells are gently scraped and then triturated with a pipette. Cells from multiple plates are combined. One plate provides enough cells for 48 wells, which is required to generate data on two complete curves for the test compound.

Uptake inhibition assay conditions: The assay is conducted in 96 1-ml vials. Krebs-HEPES (350 µl) and test compound, compounds used to define non-specific uptake, or buffer (50 µl) are added to vials and placed in a 25° C. water bath. Specific uptake is defined as the difference in uptake observed in the presence and absence of 5 µM mazindol (HEK-hDAT and HEK-hNET) or 5 µM imipramine (HEK-hSERT). Cells (50 µl) are added and preincubated with the test compound for 10 min. The assay is initiated by the addition of [$^3$H]dopamine, [$^3$H]serotonin, or [$^3$H]norepinephrine (50 µl, 20 nM final concentration). Filtration through Whatman GF/C filters presoaked in 0.05% polyethylenimine is used to terminate uptake after 10 min. The $IC_{50}$s are calculated applying the GraphPAD Prism program to triplicate curves made up of 6 drug concentrations each. Two or three independent determinations of each curve are made.

(Results)

The test compound was tested for its effects on radioligand ([$^{125}$I]RTI-55) binding to and [$^3$H]dopamine uptake by HEK cells expressing eDNA for the human dopamine transporter (HEK-hDAT cells), its effects on radioligand ([$^{125}$I]RTI-55) binding and [$^3$H]serotonin uptake by HEK cells expressing eDNA for the human serotonin transporter (HEK-hSERT cells), and its effects on radioligand ([$^{125}$I]RTI-55) binding and [$^3$H]norepinephrine uptake by HEK cells expressing eDNA for the human norepinephrine transporter (HEK-hNET cells).

In HEK-hDAT cells, the affinity of the compound for the binding site was lower than the affinity of cocaine, the standard compound, for the same site(s). The $K_i$ value for the displacement of [$^{125}$I]RTI-55 by the test compound was 14,200 nM, and the $K_i$ value for cocaine displacement of [$^{125}$I]RTI-55 binding was 236 nM. In the uptake assays test compound was less potent at blocking the uptake of [$^3$H]dopamine, with an $IC_{50}$ value of 2900 nM, as compared to the potency of cocaine ($IC_{50}$=385 nM). A Hill coefficient other than one suggests complex interactions with binding or uptake sites.

In HEK-hSERT cells, the affinity of the compound for the binding site was lower than the affinity of cocaine, the standard compound, for the same site(s). The $K_i$ value for the displacement of [$^{125}$I]RTI-55 by test compound was 81,500 nM, and the $K_i$ value for cocaine displacement, of [$^{125}$I]RTI-55 binding was 361 nM. In the uptake assays 31,827 was less potent at blocking the uptake of [3H]serotonin, with an $IC_{50}$ value greater than 100 µM, as compared to the potency of cocaine (IC50=355 nM).

In HEK-hNET cells, the affinity of the test compound for the binding site was lower than the affinity of cocaine, the standard compound, for the same site(s). The $K_i$ value for the displacement of [$^{125}$I]RTI-55 test compound was 3700 nM, and the $K_i$ value for cocaine displacement of [$^{125}$I]RTI-55 binding was 505 nM. In the uptake assays test compound was less potent at blocking the uptake of [$^3$H]norepinephrine, with an $IC_{50}$ value of 4400 nM, as compared to potency of cocaine ($IC_{50}$=194 nM). The obtained results are shown in following Table 2:

TABLE 2

Effects of test compound on HEK-hDAT, HEK-hSERT and HEK-hNET cells

| | Test Compound | Cocaine |
|---|---|---|
| HEK-hDAT cells | | |
| [$^{125}$I]RTI-55 Binding $K_i$ (nM) | 14,200 ± 3,500 | 236 ± 58 |
| Hill coefficient | −0.77 ± 0.12 | −0.83 ± 0.04 |
| [$^3$H]Dopamine Uptake $IC_{50}$ (nM) | 2900 ± 920 | 385 ± 54 |
| HEK-hSERT cells | | |
| [$^{125}$I]RTI-55 Binding $K_i$ (nM) | 81,500 ± 2,900 | 361 ± 65 |
| Hill coefficient | −2.28 ± 0.05 | −0.77 ± 0.04 |
| [$^3$H]Serotonin Uptake $IC_{50}$ (nM) | >100 µM | 355 ± 39 |

TABLE 2-continued

Effects of test compound on HEK-hDAT, HEK-hSERT and HEK-hNET cells

|  | Test Compound | Cocaine |
|---|---|---|
| HEK-hNET cells |  |  |
| [$^{125}$I]RTI-55 Binding K$_i$ (nM) | 3700 ± 1000 | 505 ± 67 |
| Hill coefficient | −1.45 ± 0.34 | −0.67 ± 0.07 |
| [$^3$H]NE Uptake IC$_{50}$ (nM) | 4400 ± 1100 | 194 ± 29 |

Numbers represent the means±SEM from at least three independent experiments, each conducted with duplicate (for binding assays) or triplicate (for uptake assays) determinations. When the K$_i$ or the IC$_{50}$ for the test compound is greater than 10 µM, only two experiments are conducted and no standard error is reported.

EXAMPLE 3

The test compound administered at 10, 30 and 100 mg/kg subcutaneously (SC) was assessed to determine the influence on spontaneous activity of wild-type and homozygous mutant dopamine transporter knockout (KO) mice. The test compound selectively reduced activity of the KO mice in a dose-dependent manner suggesting that the test compound was highly efficacious in depressing hyper motor activity in dopamine transporter KO mice.

(Methods)

Male and female wild-type and homozygous mutant dopamine transporter KO mice (n~10 mice/genotype/agent; produced by in vivo homologous recombination and bred at Duke University Medical Center, Durham, N.C.) were tested for spontaneous activity in the open field following a single injection of the vehicle or compound. Mice were placed into the open field for 30 min and administered SC the vehicle (sterile water), 2 mg/kg amphetamine, or three concentrations of the test compound (10, 30, 100 mg/kg). All drugs were given in a volume of 5 mL/kg. Animals were returned to the open field for an additional 90 min. Spontaneous activity was evaluated in an automated Omnitech Digiscan apparatus (Accuscan Instruments, Columbus, Ohio). Activity was summated at 5 min intervals over the 2 h period of testing. Horizontal activity or locomotion was measured in terms of the total distance covered in cm, vertical activity or rearing was expressed in terms of the total numbers of vertical beam breaks, and stereotypy was quantified in terms of repetitive breaks of a given beam or beams with intervals of less than sec. For the analyses, 10 WT and 10 KO mice were run in each of the treatment groups with approximately equal numbers of males and females assigned to each group. Data were analyzed by the Statistical Package for Social Sciences programs (version 11.0 for Windows; SASS Science, Chicago, Ill.). The results for each dependent variable were analyzed by repeated analyses of variance (RMANOVA) for within subjects effects (group differences over time) and between-subjects effects (tests of main effects and interactions). Bonferroni corrected pair-wise comparisons were used as the post-hoc tests. A p<0.05 was considered significant.

(Results)

Baseline: KO mice showed higher levels of locomotor, rearing and stereotypical activities compared to WT mice.

Drug Treatment: Amphetamine at 2 mg/kg SC increased locomotor, rearing and stereotypical activities in WT mice and decreased them in KO animals relative to the respective vehicle controls. The test compound reduced activities in a dose-dependent fashion and the 100 mg/kg dose suppressed activities more efficiently than amphetamine. Please see representative FIGURE below for the locomotor activity (distance traveled in cm) collapsed over the 90 min post-injection period for Amphetamine (AMPH) and test compound. Rearing and stereotyped behavior showed similar results.

The obtained results are shown in FIG. 1.

EXAMPLE 4

The effects of the test compound (15-30 mg/kg, IP) on the ability to antagonize aggressive behavior in isolated mice were examined. The test compound showed an ED$_{50}$ slightly more potent compared to imipramine in reducing isolation-induced aggression.

(Methods)

Male CD-1 mice (15-20 g) were utilized in this experiment. The test compound (15, 22 and 30 mg/kg) was dissolved in physiological saline (0.9%) and administered orally (PO) in a volume of 1 mL/100 g body weight.

Mice were isolated for up to 8 weeks in individual solid wailed wire cages (24×20×17 cm). The animals were not disturbed except to replenish food. Aggression was tested by placing an intruder mouse into the home cage of the resident animal. Aggression was characterized by an attack on the "intruder" during a three minute period. For Experimentation, following the demonstration of fighting behavior, each resident mouse was given test compound. Only those resident mice displaying fighting behavior were selected. Sixty minutes later the "intruder" was reintroduced into the home cage and the pairs were observed for the presence or absence of fighting behavior. ED$_{50}$ values were calculated from the percent inhibition of fighting in computer program hosed on probit analysis.

(Results)

The table below shows the effects of the test compound at doses of 15, 22 and 30 mg/kg on fighting behavior. There was dose-related inhibition of isolation-induced fighting behavior with an ED$_{50}$ of 25.9 mg/kg. In comparison, imipramine (30 mg/kg PO inhibited fighting behavior by 50%.

The obtained results are shown in following Table 3.

TABLE 3

Isolation-induced fighting in mice

| Treatment | Dose (mg/kg PO) | n | Inhibition of Fighting (%) | ED$_{50}$ (mg/kg, PO) (confidence limits) |
|---|---|---|---|---|
| Test Compound | 15 | 18 | 28 | 25.9 (17.7-37.9) |
|  | 22 | 18 | 44 |  |
|  | 30 | 18 | 56 |  |
| Imipramine | 15 | 10 | 20 | ~30 |
|  | 30 | 10 | 50 |  |

EXAMPLE 5

The primary objective of this study was to determine the efficacy of 2 target doses of test compound (200 and 400 mg/day) in comparison with placebo during 6 weeks of treatment in adult human subjects with moderate or severe major depression without psychotic features. An active comparator (paroxetine) was included to assist in, distinguishing a negative study from a failed study. In addition, an exit interview was intended to gather information on unexpected benefits of the test compound in order to refine the clinical development program. One or both doses of the test compound demonstrated statistically significantly greater efficacy than placebo on a broad array of secondary efficacy variables of mood and well-being, suggesting antidepressant activity for the compound. In addition, positive effects of the test compound on ratings of physical energy/fitness, reduction in sadness or depression and mental energy or motivation.

(Methods)

This was a randomized, double blind, parallel-group, active, and placebo controlled, multicenter study conducted in the U.S. (23 centers) and Canada (4 centers). There Were 2 phases: a pretreatment phase (screening/washout and a baseline visit) and a 6-week, double-blind treatment phase. Paroxetine, a positive control, was included to evaluate assay sensitivity. After washout (if needed) of prohibited substances, subjects were randomly assigned (1:1:1:1) to receive the test compound titrated to a target dose of 200 mg/day or 400 mg/day, matching placebo, or a fixed dose (20 mg/day) of parcixetine. Study drug was given twice daily for 6 weeks. Efficacy and safety were assessed weekly during the double-blind phase. Subjects completing the study underwent an Exit Interview ("Your Health and Well-Being") and completed an Assessment of Benefits of Clinical-trial Drug-treatment (ABCD) questionnaire (U.S. sites only).

(Results)

The table below summarizes the results for the primary efficacy endpoint and many of the principal secondary endpoints for the ITT (LOCF) and per-protocol (LOCF) analysis sets. Neither the 200-mg nor the 400-mg dose of the test compound was statistically significantly superior to placebo on the primary endpoint, change from baseline at Week 6 in the MADRS total score (ITT [LOCF] analysis set), although paroxetine did achieve statistically significant superiority to placebo, confirming assay sensitivity. However, 1 or both doses of test compound were statistically significantly superior to placebo or several key secondary efficacy variables at Week 6. CGI-I (200 and 400 mg), CGI-S (400 mg), MADRS response (>50% improvement in MADRS total score) (400 mg), and the sum of the apparent and reported sadness items (Items 1 and 2) of the MADRS (200 and 400 mg), suggesting antidepressant activity for the compound. Statistical significance was achieved more often in secondary analyses (across the [LOCF], per-protocol [LOCF], and ITT [observed case] analysis sets) with test compound 400 mg, but both test compound doses achieved statistically significant superiority to placebo in many analyses. In a few analyses the 200-mg dose achieved statistical significance when the 400-mg dose did not (1 item of the MADRS, 3 items of the CDS-R, 1 CDS-R cluster [ITT (LOCI) analysis set]). Thus, there was no strong evidence for a dose response relationship for test compound. Paroxetine was superior to placebo, based on the ITT (LOCF), per-protocol (LOCF), and the ITT (observed case) analysis sets, for nearly all secondary efficacy variables. On the self-rated CDS-R, only paroxetine was statistically significantly more effective than placebo (for all analysis sets). Results for test compound on the primary endpoint varied by sex: men achieved nominally statistically significant superiority to placebo at 200 mg, whereas women achieved statistically significant superiority to placebo at 400 mg. From the subject's perspective, based on the Exit Interview and the questionnaire (ABCD) on the benefits of treatment in the study (U.S. sites only), improvements in mood and well-being were, frequently experienced in all 4 treatment groups.

Paroxetine was the medication subjects preferred to take again, followed closely by test compound 200 mg. Although there were statistically significant differences between each of the active treatments and placebo on from 8 to 14 of the 51 ABCD items, there were no statistically significant differences between paroxetine and test compound (combined), or between test compound 400 mg and test compound 200 mg for any of the items on the ABCD questionnaire. The obtained results are shown in following Table 4.

TABLE 4

Selected Efficacy Results
(Intent-to-Treat [LOCF] and Per-Protocol [LOCF] Analysis Sets)

|  | | Mean Result | | | | p-Values Versus Placebo | | |
| --- | --- | --- | --- | --- | --- | --- | --- | --- |
|  | Endpoint$_a$ | Placebo (N = 117) | TC 200 mg (N = 115) | TC 400 mg (N = 120) | Paroxetine (N = 117) | TC 200 mg | TC 400 mg | Paroxetine |
| ITT (LOCF) | Primary: MADRS total score | −10.3 | −12.1 | −12.4 | −14.1 | 0.118$_b$ | 0.112$_b$ | 0.001 |
|  | Secondary: | | | | | | | |
|  | CGI-S Score | −1.0 | −1.2 | −1.3 | −1.5 | 0.061 | 0.035 | 0.002 |
|  | CGI-I Score$_c$ | —$_c$ | —$_c$ | —$_c$ | —$_c$ | 0.035 | 0.030 | <0.001 |
|  | MADRS ressponsed rate | 27% | 36% | 41% | 48% | 0.107 | 0.020 | 0.001 |
|  | MADRS remission$_d$ rate | 11% | 15% | 19% | 26% | 0.358 | 0.066 | 0.001 |
|  | MADRS sadness (Items 1 + 2) | −2.6 | −3.2 | −3.4 | −3.9 | 0.026 | 0.012 | <0.001 |
|  | MADRS core mood subscale | −6.7 | −8.6 | −8.7 | −9.7 | 0.024 | 0.022 | 0.001 |
|  | 3 Atypical items of HAM-D 31 | −0.2 | −0.4 | −0.8 | −0.6 | 0.834 | 0.078 | 0.762 |

TABLE 4-continued

Selected Efficacy Results
(Intent-to-Treat [LOCF] and Per-Protocol [LOCF] Analysis Sets)

| | | Mean Result | | | | p-Values Versus Placebo | | |
|---|---|---|---|---|---|---|---|---|
| | Endpoint[a] | Placebo (N = 117) | TC 200 mg (N = 115) | TC 400 mg (N = 120) | Paroxetine (N = 117) | TC 200 mg | TC 400 mg | Paroxetine |
| Per-Protocol (LOCF) | MADRS total score | −10.7 | −14.8 | −15.0 | −17.1 | 0.006[b] | 0.010[b] | <0.001 |
| | CGI-S score | −1.1 | −1.5 | −1.6 | −1.9 | 0.016 | 0.022 | <0.001 |
| | CGI-I score[c] | —[c] | —[c] | —[c] | —[c] | 0.004 | 0.025 | <0.001 |
| | MADRS response rate | 29% | 40% | 50% | 60% | 0.055 | 0.011 | <0.001 |
| | MADRS remission[d] rate | 14% | 20% | 29% | 35% | 0.206 | 0.037 | 0.003 |

CGI-I = Clinical Global Impressions-Improvement;
CGI-S = Clinical Global Impressions-Severity;
HAM-D 31 = 31-Item Hamilton Depression Scale;
LOCF = last observation carried forward;
MADRS = Montgomery-Asberg Depression Rating Scale.
[a]Change from baseline at Week 6.
[b]These p-values for test compound versus placebo are adjusted for multiple comparisons using Dunnett's procedure.
[c]Week 6 assessment; categorical analysis.
[d]Remission was defined as a MADRS total score less than 9.

Results from the U.S. sites of the Exit Interview and the self-rated and blinded ABCD questionnaire on the benefits of treatment in the study provided a context for interpreting the results of TC-MDD-201 from the subject's perspective. The exit interview data indicated that positive experiences most frequently included improvements in mood and well-being in ail 4 treatment groups. This was supported by data from the ABCD questionnaire, in which the most improved aspect of health during the trial was "reduction in sadness and depression". Mood, generally speaking, was the first symptom to improve, with improvement noticed mostly within the first three weeks of receiving study medication (Exit interview data).

In general, there were few differences between the 4 treatment groups within the 51 items on the ABCD questionnaire Those that were apparent were generally most robust between placebo and the active medications (i.e., "physical energy/fitness", "reduction in sadness or depression" and "mental energy or motivation") rather than between the active medications themselves. In post hoc analyses, statistically significant superiority to placebo was observed for test compound 200 nag, test compound 400 mg, and paroxetine on 14, 8, and 14 items, respectively, of the questionnaire. However, there were no statistically significant differences between test compound 400 mg and test compound 200 mg, or between paroxetine and test compound (combined scores for both doses) for any of the 51 items on the ABCD questionnaire.

References Cited

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art. Applicants reserve the right to challenge the accuracy and pertinence of the cited references.

The present invention is not to be limited in terms of the particular embodiments described in this application, which are intended has single illustrations of individual aspects of the invention. Many modifications and variations of this invention can be made without departing from its spirit and scope, as will be apparent to those skilled in the art. Functionally equivalent methods and apparatus within the scope of the invention, in addition to those enumerated herein will be apparent to those skilled in the art from the foregoing description. Such modifications and variations are intended to fall within the scope of the appended claims. The present invention is to be limited only by the terms of the appended claims, along with the full scope of equivalents to which such claims are entitled.

What is claimed is:

1. A method of diminishing manic symptoms in a mammal suffering from bipolar disorder, wherein the mammal is exhibiting manic symptoms of bipolar disorder, comprising the administration of a therapeutically effective amount of a compound having structural Formula (1) or a pharmaceutically acceptable salt thereof, to a mammal in need of treatment:

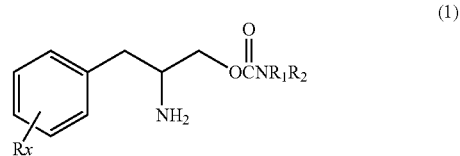

(1)

wherein,
R is selected from the group consisting of hydrogen, lower alkyl of 1 to 8 carbon atoms, halogen selected from F, Cl, Br and I, alkoxy of 1 to 3 carbon atoms, nitro, hydroxy, trifluoromethyl, and thioalkoxy of 1 to 3 carbon atoms;
x is an integer of 1 to 3, with the proviso that R may be the same or different when x is 2 or 3;
$R_1$ and $R_2$ can be the same or different from each other and are independently selected from the group consisting of hydrogen, lower alkyl of 1 to 8 carbon atoms, phenyl, and cycloalkyl of 3 to 7 carbon atoms;
or $R_1$ and $R_2$ can be joined to form a 5 to 7-membered unsubstituted heterocycle, wherein the heterocyclic compound comprises 1 to 2 nitrogen atoms and 0 to 1 oxygen atom, and the nitrogen atoms are not directly connected with each other or with the oxygen atom; to thereby diminish the manic symptoms in the mammal suffering from bipolar disorder.

2. The method of claim 1, wherein R is hydrogen.

3. The method of claim 1, wherein the compound having structural Formula (1) is an enantiomer substantially free of other enantiomers or an enantiomeric mixture wherein one enantiomer of the compound having structural Formula (1) predominates.

4. The method of claim 3, wherein one enantiomer predominates to the extent of about 90% or greater.

5. The method of claim 4, wherein one enantiomer predominates to the extent of about 98% or greater.

6. The method of claim 3, wherein the enantiomer is (S) or (L) enantiomer as represented by Structural Formula (1a):

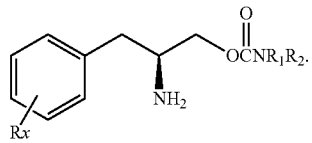

(1a)

7. The method of claim 6, wherein one enantiomer predominates to the extent of about 90% or greater.

8. The method of claim 7, wherein one enantiomer predominates to the extent of about 98% or greater.

9. The method of claim 6, wherein R is hydrogen.

10. The method of claim 3, wherein the enantiomer is (R) or (D) enantiomer, as represented by Structural Formula (1b)

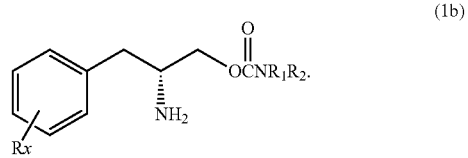

(1b)

11. The method of claim 10, wherein one enantiomer predominates to the extent of about 90% or greater.

12. The method of claim 11, wherein one enantiomer predominates to the extent of about 98% or greater.

13. The method of claim 10, wherein R is hydrogen.

* * * * *